United States Patent [19]
Mehra

[11] Patent Number: 6,081,745
[45] Date of Patent: Jun. 27, 2000

[54] METHOD AND APPARATUS FOR TREATMENT OF ARRHYTHMIAS

[75] Inventor: Rahul Mehra, Stillwater, Minn.

[73] Assignee: Medtronic, Inc., Minneapolis, Minn.

[21] Appl. No.: 09/135,480

[22] Filed: Aug. 17, 1998

[51] Int. Cl.$^7$ ........................................ A61N 1/05
[52] U.S. Cl. ........................................................ 607/4
[58] Field of Search ...................... 607/4, 5, 14

[56] References Cited

U.S. PATENT DOCUMENTS

| | | |
|---|---|---|
| 4,232,679 | 11/1980 | Schulman . |
| 4,375,817 | 3/1983 | Engle et al. . |
| 4,384,585 | 5/1983 | Zipes . |
| 4,572,191 | 2/1986 | Mirowski et al. . |
| 4,577,633 | 3/1986 | Berkovits et al. . |
| 4,587,970 | 5/1986 | Holley et al. . |
| 4,726,380 | 2/1988 | Vollmann et al. . |
| 4,727,877 | 3/1988 | Kallok . |
| 4,800,883 | 1/1989 | Winstrom . |
| 4,830,006 | 5/1989 | Haluska et al. . |
| 4,880,005 | 11/1989 | Pless et al. . |
| 4,949,719 | 8/1990 | Pless et al. . |
| 4,953,551 | 9/1990 | Mehra et al. . |
| 5,052,388 | 10/1991 | Sivula et al. . |
| 5,088,488 | 2/1992 | Markowitz et al. . |
| 5,107,850 | 4/1992 | Olive . |
| 5,117,824 | 6/1992 | Keimel et al. . |
| 5,161,527 | 11/1992 | Nappholz et al. . |
| 5,163,427 | 11/1992 | Keimel . |
| 5,188,105 | 2/1993 | Keimel . |
| 5,193,536 | 3/1993 | Mehra . |
| 5,411,524 | 5/1995 | Rahul . |
| 5,411,525 | 5/1995 | Swanson et al. . |
| 5,464,431 | 11/1995 | Adams et al. . |
| 5,486,198 | 1/1996 | Ayers et al. . |
| 5,562,709 | 10/1996 | White ............................. 607/5 |
| 5,776,164 | 7/1998 | Ripart ............................ 607/5 |
| 5,843,130 | 12/1998 | Jazayeri ......................... 607/5 |
| 5,853,426 | 12/1998 | Shieh ............................. 607/5 |
| 5,999,850 | 12/1999 | Dawson et al. ................ 607/4 |
| B1 4,232,679 | 5/1988 | Schulman . |
| B1 4,830,006 | 10/1997 | Haluska et al. . |
| B1 4,880,005 | 10/1996 | Pless et al. . |

FOREIGN PATENT DOCUMENTS

| | | |
|---|---|---|
| 9528987 | of 0000 | WIPO . |
| 9528988 | of 0000 | WIPO . |

OTHER PUBLICATIONS

U.S. Patent application, SN 08/649,145, filed May 14, 1996 by Gillberg et al, for Prioritized Rul Based Method and Apparatus for Diagnosis and Treatment of Arrhythmias.

"Synchronous Intracardiac Cardioversion", by Zipes et al., published in *Modern Cardiac Pacing*, edited by Barold, Futura Publishing Co. 1985, pp. 727–743.

*Primary Examiner*—Jeffrey R. Jastrzab
*Attorney, Agent, or Firm*—Reed A. Duthler; Harold R. Patton

[57] ABSTRACT

An atrial cardioverter and a method of its operation. The cardioverter measures an interval between successive R-waves, defines a ventricular escape interval as a function of the measured interval between successive R-waves and delivers a ventricular pacing pulse at the expiration of the ventricular escape interval in the absence of R-waves during the ventricular escape interval. The cardioverter defines a synchronization interval following delivery of the ventricular pacing pulse, and delivers an atrial cardioversion pulse synchronized to an R-wave occurring after expiration of the synchronization interval, absent R-waves during the synchronization interval.

16 Claims, 6 Drawing Sheets

METHOD AND APPARATUS FOR TREATMENT OF ARRHYTHMIAS

BACKGROUND OF THE INVENTION

This invention relates to devices which treat tachyarrhythmias (rapid heart rhythms), and more specifically, to methods to provide delivery of atrial cardioversion and defibrillation shocks at appropriate times relative to atrial and ventricular depolarizations.

It has long been recognized that synchronizing atrial and ventricular cardioversion to depolarizations in the chamber being treated improves efficacy of treatment. For example, synchronization of ventricular cardioversion shocks to sensed R-waves is disclosed in U.S. Pat. No. 4,375,817 issued to Engle et al. Synchronization of cardioversion shocks intended to treat atrial or ventricular tachycardia or fibrillation to detected R-waves is disclosed in U.S. Pat. No. 4,384,585, issued to Zipes. Synchronization of atrial cardioversion shocks to detected P-waves is disclosed in U.S. Pat. No. 4,572,191, issued to Mirowski et al.

Delivery of cardioversion or defibrillation shocks intended to terminate a tachyarrhythmia of one chamber unfortunately may induce a tachyarrhythmia in the other chamber. The risk associated with tachyarrhythmia induction in the ventricle is sufficiently great that it has long been recognized that atrial defibrillation pulses need to be timed to avoid the vulnerable period of the ventricle. The most common approach to accomplish this result has been to deliver the atrial defibrillation or cardioversion pulse closely synchronized to a sensed ventricular depolarization to avoid the associated ventricular vulnerable period, as disclosed in U.S. Pat. No. 4,384,585, issued to Zipes. It has also long been recognized that the vulnerable period following a ventricular depolarization may extend to include the time of occurrence of the next subsequent ventricular depolarization in the presence of a sufficiently rapid ventricular rhythm. In such cases, there is no safe time for delivery of a cardioversion pulse, as discussed in the article "Synchronous Intracardiac Cardioversion", by Zipes et al., published in *Modern Cardiac Pacing*, edited by Barold, Futura Publishing Co. 1985, pages 727–743.

Because cardioversion pulses synchronized to a ventricular rhythm which is too rapid may induce ventricular arrhythmias or fibrillation, implantable cardioverters have typically included some method to assure that a minimum R-R interval has elapsed as a prerequisite to delivery of a cardioversion shock. One such synchronization method which prevents delivery of a cardioversion pulse synchronized to a ventricular rhythm which is too rapid is to require that the shock be synchronized to a ventricular depolarization falling outside a defined refractory period defined following the immediately preceding ventricular depolarization, as in the Model 7210 implantable transvenous cardioverter manufactured by Medtronic, Inc. While this device could sense ventricular depolarizations during this refractory period and would initiate a new refractory period following such depolarizations, it would not deliver cardioversion pulses synchronized to such depolarizations. As reflected in the above-cited article by Zipes et al, the transvenous cardioversion therapy provided by the model 7210 device could be employed to treat either ventricular or supraventricular tachyarrhythmias.

A more sophisticated method of synchronization to sensed R-waves is set forth in U.S. Pat. No. 5,486,198, in which a shock is delivered synchronized to an R-wave only if the R—R interval between the R-wave and the immediately preceding R-wave is greater than or no more than a defined amount less than the immediately preceding R—R interval. This method of synchronization to sensed R-waves, like those discussed above, unfortunately does not allow safe delivery of an atrial cardioversion shock in the presence of too rapid a ventricular rate.

An alternative method for preventing delivery of an atrial cardioversion shock during the ventricular vulnerable period is to deliver the shock after a defined interval following a preceding R-wave, in the absence of an intervening sensed ventricular depolarization, the defined interval being sufficiently long to prevent delivery during the vulnerable period associated with the preceding R-wave. Such a synchronization method is disclosed in U.S. Pat. No. 5,411,524, issued to Mehra. As disclosed in the Mehra patent, the defined interval may vary as a function of the sensed ventricular rate, but it must be greater than a predefined minimum duration and thus is also unavailable in the presence of too rapid a ventricular rate.

An additional method for avoiding delivery of a cardioversion pulse during the vulnerable period of a chamber of the heart is to pace the chamber and deliver the cardioversion pulse in the refractory period following the pacing pulse. One such approach is also disclosed in U.S. Pat. No. 5,411,524 issued to Mehra, wherein an atrial cardioversion pulse is synchronized to a single ventricular pacing pulse and in U.S. Pat. No. 5,193,536, also issued to Mehra, wherein a ventricular cardioversion pulse is synchronized to the last of a series of ventricular pacing pulses. In both cases, the ventricular pacing pulse escape interval is calculated to be less than the intervals separating intrinsic ventricular depolarizations. These methods, unfortunately are not necessarily useful in the case of a ventricular rhythm so rapid that synchronization to an overdrive ventricular pacing pulse is unsafe.

SUMMARY OF THE INVENTION

The present invention provides an implantable atrial defibrillator which provides for safe delivery of atrial cardioversion pulses even in the presence of a ventricular rate so rapid it would otherwise preclude safe atrial cardioversion. The device takes advantage of the phenomenon similar to one observed in bradycardia pacing, turning it to a new use in the context of an atrial cardioversion synchronization method. In bradycardia pacing it has been observed that delivery of a an overdrive ventricular pacing pulse closely timed to a sensed R-wave causes a prolonged R—R interval thereafter, much like the compensatory pause following a PVC. It has been determined by the inventor that this phenomenon manifests itself even in the presence of atrial fibrillation. This fact in turn has allowed the development of an atrial cardioversion synchronization method which allows safe delivery of atrial cardioversion pulses in the presence of very rapid ventricular rates.

A device employing the method of the present invention measures the intervals separating R-waves in the presence of atrial fibrillation and calculates a shorter ventricular pacing escape interval, similar to the method described in the above-cited Mehra '524 patent, on expiration of which a ventricular pacing pulse is delivered. However, rather than delivering an atrial cardioversion pulse synchronized to the delivered ventricular pacing pulse, the device relies upon the expected extended intrinsic R—R interval following the delivered pacing pulse and defines a synchronization interval following the delivered pacing pulse which is longer than the previous ventricular pacing escape interval, and which may also be longer than the previous intrinsic R—R intervals. The device delivers an atrial cardioversion pulse thereafter on occurrence of the next sensed R-wave, provided it occurs after expiration of the synchronization interval. In some embodiments of the invention the device may deliver a cardioversion pulse alone or in conjunction with a delivered ventricular pacing pulse on expiration of a lower rate interval longer than the synchronization interval, in the absence of a sensed R-wave.

The inventive synchronization method, although similar in some respects to each of the synchronization methods described above, provides a result unobtainable with any of the above described methods. Because the overdrive ventricular pacing pulse need not trigger an R-wave which itself may be safely employed for synchronized delivery of an atrial cardioversion pulse, it may be delivered in circumstances where the synchronization method of the Mehra '524 patent could not be safely employed. Because the delivered overdrive ventricular pacing pulse triggers an increased intrinsic R—R interval, a relatively long synchronization interval can be employed to allow safe delivery of atrial cardioversion pulses even in the presence of a ventricular rate which normally would be too rapid to allow for safe delivery of synchronized atrial cardioversion.

DETAILED DESCRIPTION OF THE PREFERRED EMBODIMENTS

Figure 1:
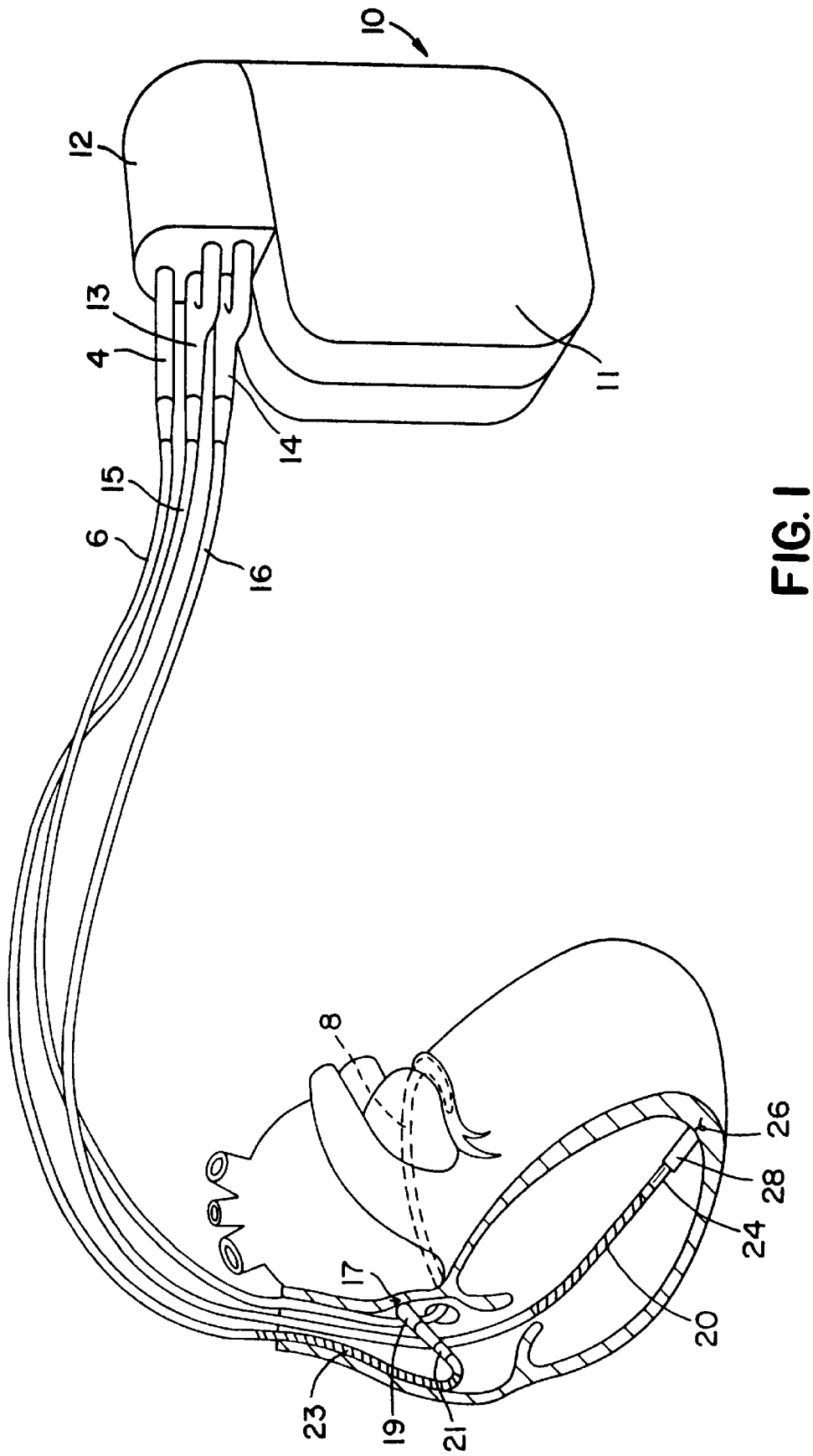
FIG. 1 illustrates a first embodiment of an implantable pacemaker/cardioverter/defibrillator of a type appropriate for use in practicing the present invention, in conjunction with a human heart.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coiled defibrillation electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 which carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding generally to the structure of the ventricular lead. Located adjacent the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coiled defibrillation electrode 23 is provided, proximal to electrode 21 and coupled to the third conductor within the lead body 15. Electrode 23 preferably is 5 cm in length or greater and is configured to extend from the SVC toward the tricuspid valve. At the proximal end of the lead is a bifurcated connector 13 which carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 which carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using a plastic coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may of course be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
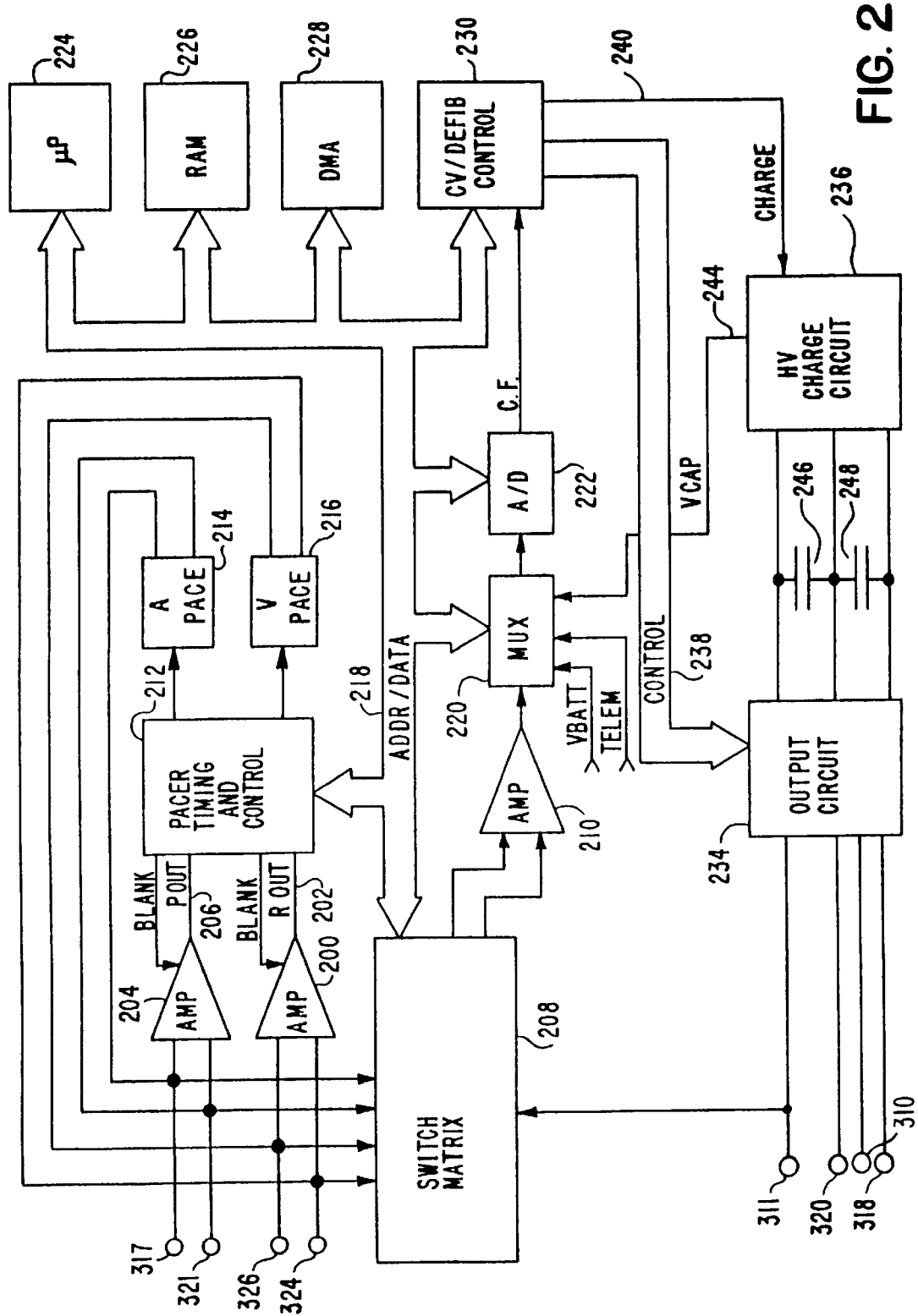
FIG. 2 illustrates a functional schematic diagram of an implantable pacemaker/cardioverter/defibrillator in which the invention may be practiced.

FIG. 2 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices providing therapies for treating atrial arrhythmias only and cardioverters and defibrillators which do not provide antitachycardia pacing therapies, and devices which deliver additional forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/ defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204. which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with antitachyarrhythmia pacing in both the atrium and the ventricle, employing, any antitachyarrhythmia pacing therapies known to the art.

Intervals defined by pacer timing/control circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to circuitry 212 via address/data bus 218. Pacer timing/control circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including antitachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, operating under control of programming stored in its read only memory and is responsive to interrupts from pacer timing/control circuitry 212 corresponding to the occurrences of sensed P-waves and R-waves and corresponding to the generation of cardiac pacing pulses and cardioversion/defibrillation pulses. These interrupts are provided via data/address bus 218. Any necessary mathematical calculations to be per-formed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The present invention may employ any tachycardia detection algorithm known to the art to detect the occurrence of tachyarrhythmias. For example, the detection methods disclosed in U.S. Pat. No. 5,545,186 issued to Olson et al for detection of atrial fibrillation and tachycardias may be employed, or the method of U.S. patent application Ser. No. 08/649,145 fled May 14, 1996 by Gillberg et al, may be substituted for this detection method. The Olson patent and the Gillberg et al. application are hereby incorporated by reference in their entireties. Alternatively, other known detection algorithms for use in conjunction with implantable atrial cardioverters such as those disclosed in U.S. Pat. No. 5,464,431 issued to Adams et al, U.S. Pat. No. 5,161,527 issued to Nappholz et al, or U.S. Pat. No. 5,107,850 issued to Olive, all incorporated by reference in their entireties may also be employed. A device embodying the present invention may also include the ability to treat ventricular tachyarrhythmias, as discussed above. In the event such capability is desired, any of the prior art ventricular tachyarrhythmia detection methods may be employed, including those in the above cited Olson patent and Gillberg et al application, as well as the detection methods disclosed in U.S. Pat. No. 5,620,471 issued to Duncan, U.S. Pat. No. 4,830,006 issued to Haluska et al., U.S. Pat. No. 4,880,005 issued to Pless et al., and U.S. Pat. No. 5,560,369 issued to McClure et al., all incorporated by reference in their entireties as well. In addition, the device may be configured such that the patient initiates delivery of the therapy by means of an external controller, such that the device may not employ a detection method of its own as a prerequisite to a delivery of therapy. In this context, a patient activator as disclosed in U.S. patent application Ser. No. 08/764,865 by Prieve et al. filed on Dec. 16, 1996, incorporated by reference in its entirety herein may be employed. Alternatively, patient activators of the sort disclosed in U.S. Pat. No. 5,674,249 issued to DeCoriolis et al. or U.S. Pat. No. 4,263,679 issued to Schulman, all incorporated by reference in their entireties may instead be employed. The particular choice of patient activator is not critical to the success of the invention, and any workable method for initiating the delivery of the atrial cardioversion or defibrillation therapy may usefully be employed.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing/control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 4,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counters in circuitry 212 to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. Any known ventricular cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed. In addition, high frequency pulse bursts may be delivered to electrodes 317 and 321 to terminate atrial tachyarrhythmias, as described in PCT Patent Publication No. WO95/28987, filed by Duffin et al and PCT Patent Publication No. WO95/28988, filed by Mehra et al, both incorporated herein by reference in their entireties.

In the illustrated device, delivery of cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above cited patent issued to Mehra and in U.S. Pat. No. 4,726,877, incorporated by reference in its entirety.

An example of circuitry which may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the particular therapies are programmed into the device ahead of time by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al.

Figure 3:
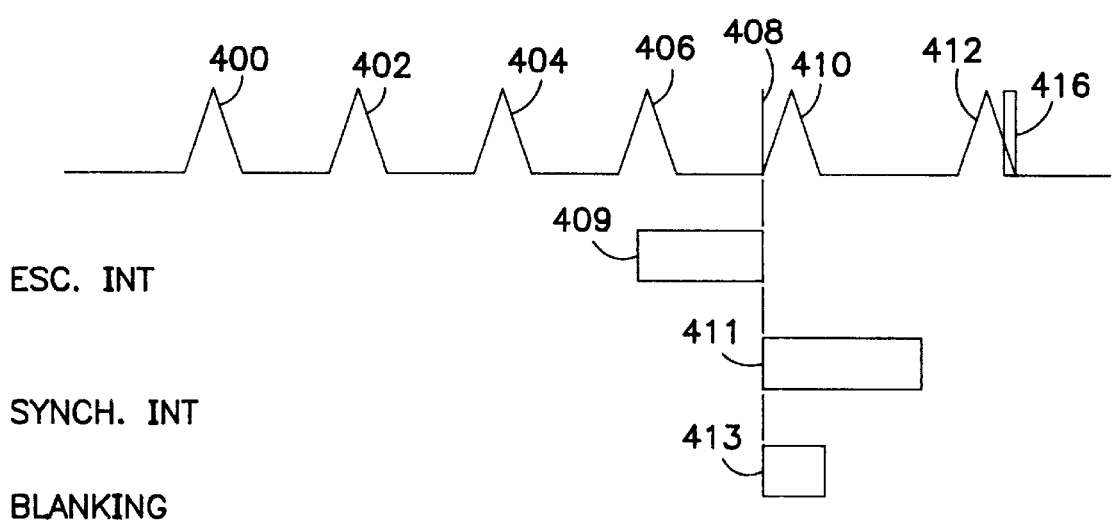
FIG. 3 illustrates the synchronization method used by a device embodying the present invention.

FIG. 3 is a simulated electrogram and timing diagram illustrating the synchronization method of the present invention. In interpreting the simulated electrogram, it should be understood that atrial fibrillation is ongoing. Atrial depolarizations are not illustrated, for the sake of simplicity. A rapid ventricular rhythm, including R-waves 400, 402, 404 and 406 is underway, for example separated by intervals of less than 400 milliseconds. After charging the high voltage output capacitors, the device of FIG. 2 measures the R—R intervals between R-waves 400, 402, 404 and 406 to derive a ventricular escape interval which is shorter than the preceding R—R intervals. At the expiration of the escape interval 409, a ventricular pacing pulse 408 is delivered, triggering an R-wave 410. Simultaneous with delivery of the pacing pulse 408, the device initiates a synchronization interval 411 which may extend, for example, for 400 milliseconds or more after delivery of pacing pulse 408. A blanking period or refractory period 413 is also initiated following pacing pulse 408.

Delivery of pacing pulse 408, triggering R-wave 410 causes a delay in the occurrence of the next subsequent R-wave 412 until after expiration of the synchronization interval 411. On sensing of an R-wave 412, after expiration of the synchronization interval, the device delivers an atrial cardioversion pulse 416, safely outside the refractory period of R-wave 410. In the event that an R-wave is sensed during synchronization interval 411, after blanking or refractory period 413, the device will reinitiate the synchronization sequence, measuring the V-R interval separating pacing pulse 408 and the sensed R-wave and defining a new escape interval based on the V-R interval and preceding R—R intervals. If the device is unable to successfully synchronize using the synchronization method illustrated, it may repeat the synchronization sequence. On failure to successfully deliver a synchronized cardioversion or defibrillation pulse within a predetermined maximum time period or within a predetermined number of delivered overdrive pacing pulses, the device aborts the attempt at cardioversion therapy and returns to normal bradycardia pacing.

The synchronization method of the present invention may be the only synchronization method employed by the device. However, it is anticipated that it more likely will be included in the device along with one or more alternative synchronization methods. The synchronization method of the present invention may be employed, for example, in response to failure to synchronize using an alternative synchronization method or in response to a heart rhythm determined to be inappropriate for employing an alternative synchronization method.

Figure 4:
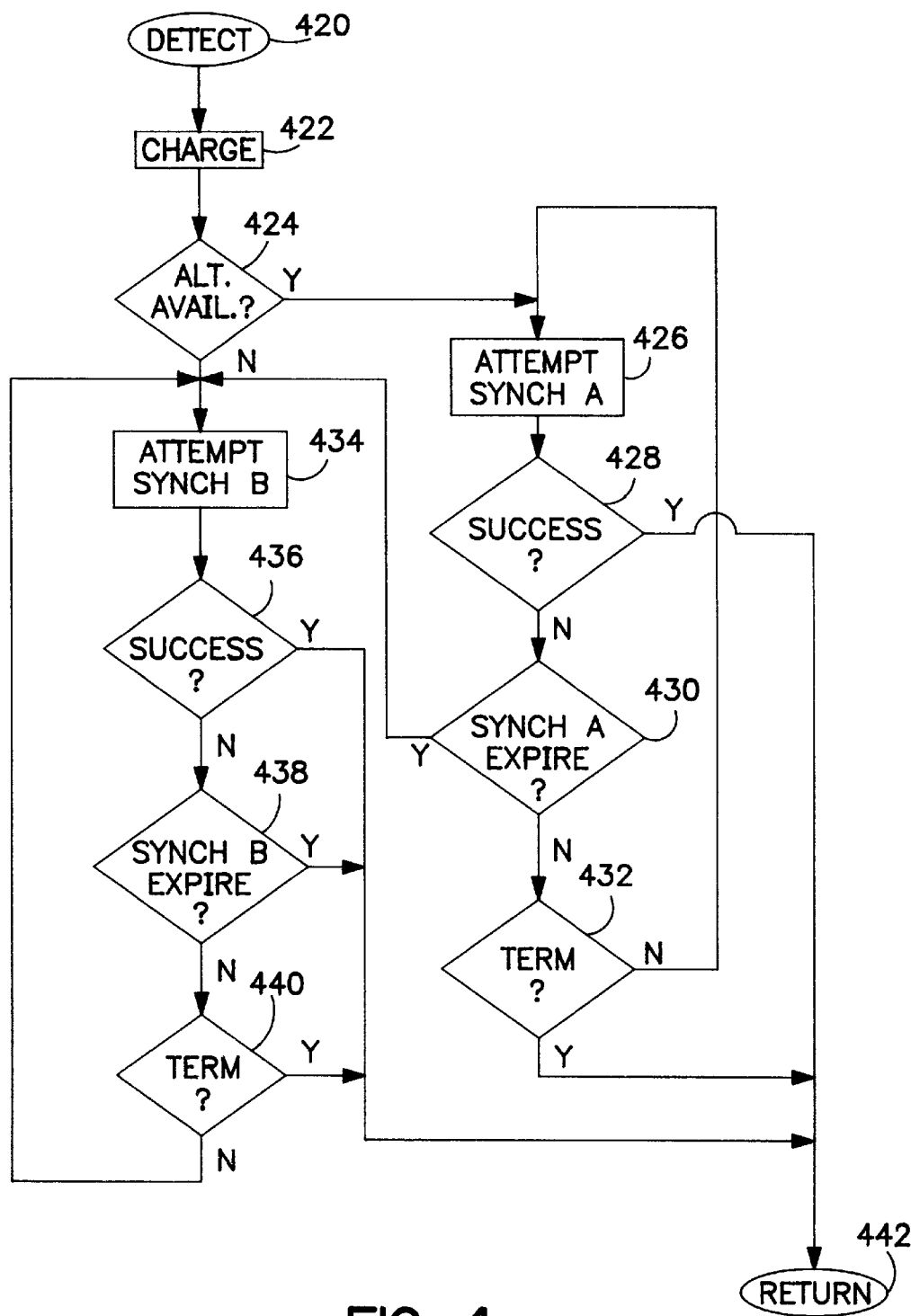
FIG. 4 is a functional flowchart illustrating a first embodiment of the operation of the synchronization method of a preferred embodiment of a device according to the present invention.

FIG. 4 is a functional flow chart illustrating a first method of operation of the device of FIGS. 1 and 2 in response to detection of an atrial tachyarrhythmia requiring delivery of a cardioversion or defibrillation pulse. After detection of atrial tachyarrhythmia at 420, the device charges its high voltage output capacitors, and on completion of capacitor charging attempts to deliver a ventricular synchronized atrial cardioversion shock. The device may optionally first attempt synchronization using an alternative method, referred to in FIG. 4 as "Synch A" which may be any of the numerous known synchronization methods for atrial cardioversion. For example, the device may simply define a minimum R—R interval as prerequisite to cardioversion as described in U.S. Pat. No. 5,411,524 issued to Keimel, or may use any of the various other cardioversion mechanisms described in U.S. Pat. No. 5,486,198, U.S. Pat. No. 5,411,525 and U.S. Pat. No. 5,193,536, all incorporated herein by reference in their entireties. If an alternative cardioversion mechanism is not available or is not enabled at 424, the device proceeds immediately to attempt synchronization using the cardioversion synchronization method of the present invention, referred to in FIG. 4 as "Synch B".

Assuming that an alternative cardioversion synchronization method is available at 424, the device attempts to deliver a synchronized atrial cardioversion shock at 426 using the alternative synchronization method. The device continues to attempt to deliver a synchronized atrial cardioversion shock using the alternative synchronization method until expiration of a first maximum time period (e.g. 30 seconds to 3 minutes) or a predetermined number of synchronization attempts (e.g. 2–20) at 430, or until spontaneous termination of the detected atrial tachyarrhythmia at 432. If the device is successful in delivering an atrial cardioversion shock using the alternative synchronization method "Synch A" or if the tachyarrhythmia terminates, the device returns to bradycardia pacing at 442.

If the maximum interval for synchronization employing the alternative synchronization method "Synch A" expires or the maximum number of attempts occur prior to successful delivery of a synchronized atrial cardioversion shock, the device attempts synchronization at 434 using the synchronization method "Synch B" of the present invention. The device continues to attempt to deliver a synchronized cardioversion shock using the method of the present invention until a cardioversion shock is successfully delivered at 436 or a second maximum synchronization time period for synchronization using the method of the present invention (e.g. 30 seconds to 3 minutes) or a predetermined number of synchronization attempts (e.g. 2–20) at 438 or until spontaneous termination of the atrial tachyarrhythmia is detected at 440. Following any of these events, the device returns to bradycardia pacing at 442.

Figure 5:
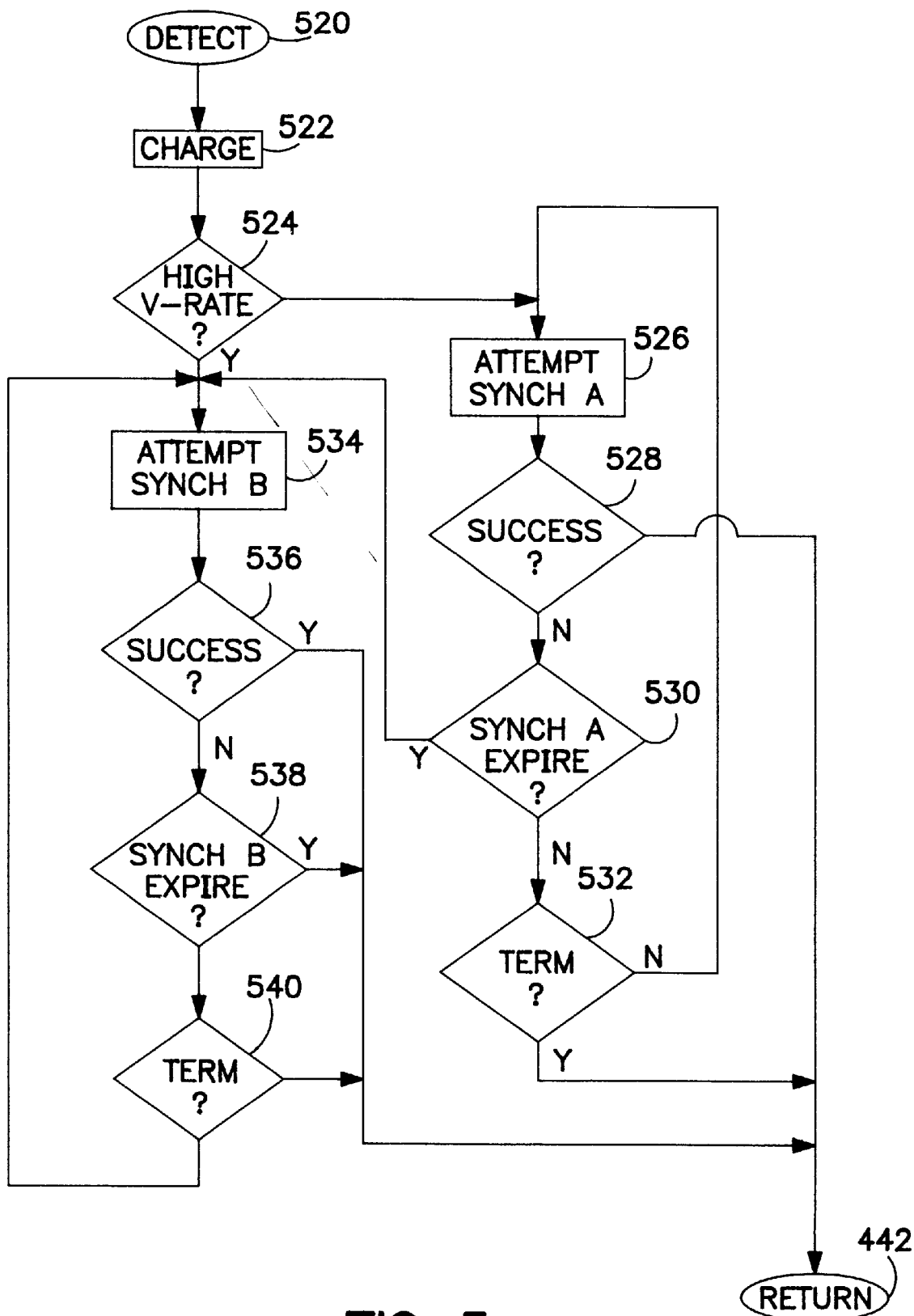
FIG. 5 is a functional flowchart illustrating a second embodiment of the operation of the synchronization method of a preferred embodiment of a device according to the present invention.

FIG. 5 is a functional flow chart illustrating a second method of operation of the device of FIGS. 1 and 2 in response to detection of an atrial tachyarrhythmia requiring delivery of a cardioversion or defibrillation pulse. After detection of atrial tachyarrhythmia at 520, the device charges its high voltage output capacitors, and on completion of capacitor charging attempts to deliver a ventricular synchronized atrial cardioversion shock. The device then determines at 524 whether synchronization with an alternative synchronization method, referred to in FIG. 5 as "Synch A" is appropriate. "Synch A" may be any of the numerous known synchronization methods for atrial cardioversion, as described above in conjunction with FIG. 4. The device may determine that the alternative synchronization method "Synch A" is appropriate at 524, for example, if the ventricular rate is not an excessively high rate. A determination that the ventricular rate is excessively high may be made, for example, in response to a series of R-waves separated by V—V intervals all less than a defined duration such as 300–400 ms. or in response to a series of R-waves separated by V—V intervals averaging less than a defined duration such as 300–400 ms. If the alternative cardioversion mechanism is not appropriate, the device proceeds immediately to attempt synchronization using the cardioversion synchronization method of the present invention, referred to in FIG. 5 as "Synch B".

Assuming that an alternative cardioversion synchronization method is determined to be appropriate at 524, the device attempts to deliver a synchronized atrial cardioversion shock at 526 using the alternative synchronization method, and continues to attempt to deliver a synchronized atrial cardioversion shock using the alternative synchronization method until expiration of a first maximum time period or a predetermined number of synchronization attempts at 530 or until spontaneous termination of the detected atrial tachyarrhythmia at 532. Alternatively, prior to each re-attempt at synchronization using the alternative synchronization method at 526, the device may determine at 524 whether the ventricular rhythm remains appropriate for employing the alternative synchronization method and, if not, switch the synchronization method "Synch B" of the present invention.

If the device is successful in delivering an atrial cardioversion shock using the alternative synchronization method "Synch A", or if the tachyarrhythmia terminates at 532, the device returns to normal pacing at 542. If the maximum interval for synchronization employing the alternative synchronization method "Synch A" expires or the maximum number of synchronization attempts are made prior to successful delivery of a synchronized atrial cardioversion shock, the device may thereafter attempt synchronization at 434 using the synchronization method "Synch B" of the present invention or alternatively may simply return to bradycardia pacing at 442.

If the alternative synchronization method is inappropriate at 524 of if it fails to successfully deliver a synchronized cardioversion shock, the device attempts to deliver a synchronized cardioversion shock using the method of the present invention at 534. The device continues to attempt to deliver a synchronized cardioversion shock using the synchronization method of the present invention (Synch B) until a cardioversion shock is successfully delivered at 436 or until expiration of a second maximum synchronization time period or a second maximum number of synchronization attempts at 438 or until spontaneous termination of the atrial tachyarrhythmia is detected at 440. Following any of these events, the device returns to bradycardia pacing at 442.

Figure 6:
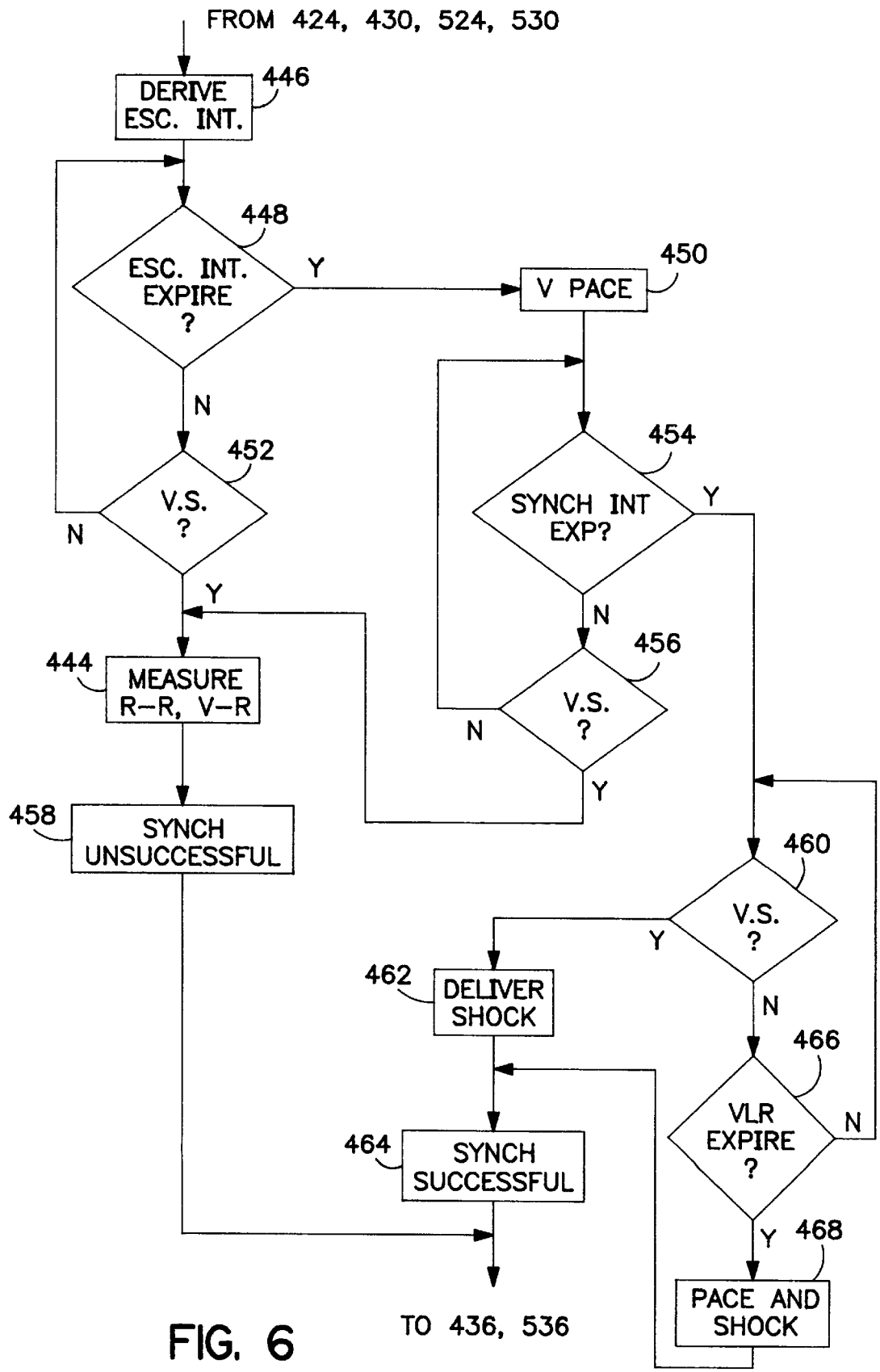
FIG. 6 is a functional flowchart illustrating details of the operation of the synchronization method of the present invention.

FIG. 6 is a functional flow chart illustrating the operation of the synchronization method of the present invention in more detail. The flow chart corresponds to the functional boxes labeled 434 and 534 in FIGS. 4 and 5 respectively, and is entered in response to a determination that either the alternative synchronization mechanism "Synch A" is not available or appropriate at 424 or 524 or in response to expiration of the maximum time period or maximum number of synchronization attempts available for "Synch A" at 430 or 530. In response, the device measures the duration of one or more preceding R—R and V-R intervals at 444 and derives a ventricular escape interval at 446. The ventricular escape interval may be, for example, a percentage of the average R—R intervals over one or more R—R intervals or may be equal to a percentage of the shortest of R—R intervals over one or more preceding R—R intervals. In either case, the intent is to define a ventricular escape interval short enough that it is highly likely that the escape interval will expire before the next sensed R-wave. At 448, the device checks to see if the escape interval has timed out. If not, the device checks at 452 to determine whether a ventricular sensed event has occurred. This process occurs until either time out of the escape interval at 448 or sensing at an R-wave at 452. In the event that an R-wave is sensed at 452 prior to expiration of the escape interval, the device measures the R—R interval at 444, notes that the synchronization attempt was unsuccessful at 458 and the device returns to the flow chart of FIG. 4, to determine whether the maximum interval for synchronization has expired or the maximum number of synchronization attempts has been reached or the underlying arrhythmia has terminated. If not, the device will initiate a new synchronization sequence, employing the newly measured R—R interval at 444 and calculating a new escape interval at 446. Assuming the escape interval times out at 448, a ventricular pacing pulse is delivered at 450, with the intent of triggering the ventricular depolarization. The device then waits until either expiration of the synchronization interval at 454 or sensing a ventricular depolarization at 456. In the event that a ventricular depolarization is sensed at 456, after the blanking or refractory period and prior to expiration of the synchronization interval, the device measures the V-R interval at 444, notes that the synchronization attempt was unsuccessful at 458, and will again initiate a new synchronization attempt using the V-R interval measured at 494 to calculate a new escape interval at 446, assuming that the arrhythmia is still present and the maximum period for synchronization using the method of the present invention has not expired.

On expiration of the synchronization interval at 454 without a preceding sensed ventricular event, the device then awaits occurrence of a ventricular sensed event at 460 or expiration of a ventricular lower rate period at 456, which may be, for example, equal to the bradycardia pacing rate of the device. In response to a sensed R-wave after the expiration of the synchronization interval, and prior to expiration of the lower rate interval, the device delivers a cardioversion shock at 462, and indicates that the synchronization method has been successful at 464. The device thereafter returns to bradycardia pacing operation and attempts to determine whether or not the cardioversion shock terminated the detected atrial tachyarrhythmia.

If the ventricular lower rate interval times out at 466 without a prior sensed ventricular depolarization, the device delivers a ventricular pacing pulse at 468 and a cardioversion shock synchronized to the delivered ventricular pacing pulse. Alternatively, the device may simply deliver a cardioversion shock on expiration of the lower rate interval at 466. The device notes that the synchronization method was successful at 464, and the device returns to bradycardia pacing and attempts to determine whether or not the delivered cardioversion pulse was successful in terminating the detected atrial tachyarrhythmia.

In the above described embodiments, the device provides a single overdrive ventricular pacing pulse prior to timing the synchronization interval. It should also be understood that the device may alternatively deliver a series of two or more ventricular pacing pulses at the defined escape interval prior to initiating the synchronization interval. In addition, the device is described as providing a ventricular pacing pulse and cardioversion pulse or a cardioversion pulse alone on expiration of a lower rate interval which corresponds to the base pacing rate, which interval typically would be significantly longer than the synchronization interval. However, this interval may instead deliver the cardioversion shock on expiration of an interval significantly less than the interval corresponding to the base pacing rate, for example extending only 100–200 ms after the synchronization interval.

The above disclosure sets forth a device in which sensed events in the atrium and ventricle are used to control delivery of electrical therapy to treat tachyarrhythmias. Although it seems likely that commercial embodiments of such a device will require the use of a microprocessor in order to perform the numerous calculations and analysis steps required, it is within the realm of possibility that some or all of the detection criteria provided by the microprocessor in the above disclosure might instead be provided by means of a full custom, integrated circuit, particularly a circuit in which a state counter is employed instead of stored software, in order to control sequential operation of the digital circuitry, along the general lines of the circuits disclosed in U.S. Pat. No. 5,088,488, issued to Markowitz et al. and U.S. Pat. No. 5,052,388, issued to Sivula et al., both of which are incorporated herein by reference in their entireties. Thus, the above description should be considered exemplary, rather than limiting, with regard to the interpretation of the following claims.

In conjunction with the above disclosure, we claim:

1. An atrial cardioverter, comprising:
   means for measuring an interval between successive R-waves, means for defining a ventricular escape interval as a function of the measured interval between successive R-waves, means for delivering a ventricular pacing pulse at the expiration of the ventricular escape interval in the absence of R-waves during the ventricular escape interval, means for defining a synchronization interval following delivery of the ventricular pacing pulse, and means for delivering an atrial cardioversion pulse synchronized to an R-wave occurring after expiration of the synchronization interval, absent R-waves during the synchronization interval.

2. A cardioverter according to claim 1, further comprising means for defining an extended time interval longer than the synchronization interval, following delivery of the ventricular pacing pulse and means for delivering an atrial cardioversion pulse in response to expiration of the extended time interval.

3. A cardioverter according to claim 1, further comprising means for defining an extended time interval longer than the synchronization interval, following delivery of the ventricular pacing pulse and means for delivering an additional ventricular pacing pulse and an atrial cardioversion pulse in response to expiration of the extended time interval.

4. A method of atrial cardioversion, comprising:
   measuring an interval between successive R-waves, defining a ventricular escape interval as a function of the measured interval between successive R-waves, delivering a ventricular pacing pulse at the expiration of the ventricular escape interval absent R-waves during the ventricular escape interval, defining a synchronization interval following delivery of the ventricular pacing pulse, and delivering an atrial cardioversion pulse synchronized to an R-wave occurring after expiration of the synchronization interval, absent R-waves during the synchronization interval.

5. A method according to claim 4, further comprising the steps of defining an extended time interval longer than the synchronization interval, following delivery of the ventricular pacing pulse and delivering an atrial cardioversion pulse in response to expiration of the extended time interval.

6. A method according to claim 4, further comprising the steps of defining an extended time interval longer than the synchronization interval, following delivery of the ventricular pacing pulse and delivering an additional ventricular pacing pulse and an atrial cardioversion pulse in response to expiration of the extended time interval.

7. An atrial cardioverter, comprising:
   means for delivering R-wave synchronized atrial defibrillation pulses according to a first synchronization method, means for delivering R-wave synchronized atrial defibrillation pulses according to a second synchronization method and means for selecting between said first and second synchronization methods; wherein the means for delivering R-wave synchronized atrial defibrillation pulses according to a first synchronization method in turn comprises;
      means for measuring an interval between successive R-waves, means for defining a ventricular escape interval as a function of the measured interval between successive R-waves, means for delivering a ventricular pacing pulse at the expiration of the ventricular escape interval absent R-waves during the ventricular escape interval, means for defining a synchronization interval following delivery of the ventricular pacing pulse, and means for delivering an atrial cardioversion pulse synchronized to an R-wave occurring after expiration of the synchronization interval, absent R-waves during the synchronization interval.

8. A cardioverter according to claim 7, wherein the means for delivering R-wave synchronized atrial defibrillation pulses according to a first synchronization method further comprises means for defining an extended time interval longer than the synchronization interval, following delivery of the ventricular pacing pulse and means for delivering an atrial cardioversion pulse in response to expiration of the extended time interval.

9. A cardioverter according to claim 7, wherein the means for delivering R-wave synchronized atrial defibrillation pulses according to a first synchronization method further comprises means for defining an extended time interval longer than the synchronization interval, following delivery of the ventricular pacing pulse and means for delivering an additional ventricular pacing pulse and an atrial cardioversion pulse in response to expiration of the extended time interval.

10. A cardioverter according to claim 7, wherein the selecting means comprises means for measuring R-wave rates means responsive to a rapid R-wave rate for selecting the first synchronization method.

11. A cardioverter according to claim 7, wherein the selecting means comprises means for determining whether operation of the means for delivering R-wave synchronized atrial defibrillation pulses according to a second synchronization method results in delivery of an atrial cardioversion pulse and means responsive to failure of the means for delivering R-wave synchronized atrial defibrillation pulses according to a second synchronization method to deliver an atrial cardioversion pulse for selecting the first synchronization method.

12. A method of atrial cardioversion, comprising:
   defining first and second synchronization methods, selecting between first and second synchronization methods and employing the selected synchronization method, wherein the first synchronization method comprises;
   measuring an interval between successive R-waves, defining a ventricular escape interval as a function of the measured interval between successive R-waves, delivering a ventricular pacing pulse at the expiration of the ventricular escape interval absent R-waves during the ventricular escape interval, defining a synchronization interval following delivery of the ventricular pacing pulse, and delivering an atrial cardioversion pulse synchronized to an R-wave occurring after expiration of the synchronization interval, absent R-waves during the synchronization interval.

13. A method according to claim 12, wherein the first synchronization method further comprises defining an extended time interval longer than the synchronization interval, following delivery of the ventricular pacing pulse and delivering an atrial cardioversion pulse in response to expiration of the extended time interval.

14. A method according to claim 12, wherein the first synchronization method further comprises defining an extended time interval longer than the synchronization interval, following delivery of the ventricular pacing pulse and delivering an additional ventricular pacing pulse and an atrial cardioversion pulse in response to expiration of the extended time interval.

15. A method according to claim 12, wherein the selecting step comprises measuring R-wave rates means and, responsive to a rapid R-wave rate, selecting the first synchronization method.

16. A cardioverter according to claim 12, wherein the selecting step comprises determining whether the second synchronization method results in delivery of an atrial cardioversion pulse and, responsive to failure of second synchronization method to deliver an atrial cardioversion pulse, selecting the first synchronization method.

\* \* \* \* \*